(12) United States Patent
Struble et al.

(10) Patent No.: US 8,396,549 B2
(45) Date of Patent: Mar. 12, 2013

(54) PAPILLARY MUSCLE STIMULATION

(75) Inventors: Chester W. Struble, Eijsden (NL); Frits W. Prinzen, Maastricht (NL); Pierre A. Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 1172 days.

(21) Appl. No.: 10/834,899

(22) Filed: Apr. 28, 2004

(65) Prior Publication Data

US 2004/0230236 A1 Nov. 18, 2004

Related U.S. Application Data

(63) Continuation-in-part of application No. 10/360,765, filed on Nov. 29, 2001, now abandoned.

(51) Int. Cl.
*A61N 1/36* (2006.01)
(52) U.S. Cl. ............................ 607/4; 607/14; 607/123
(58) Field of Classification Search ................ 607/4, 9, 607/14, 123, 129–131
See application file for complete search history.

(56) References Cited

U.S. PATENT DOCUMENTS

| | | |
|---|---|---|
| 3,857,399 A | 12/1974 | Zacouto |
| 4,928,688 A | 5/1990 | Mower |
| 5,095,916 A | 3/1992 | Smits |
| 5,267,560 A | 12/1993 | Cohen |
| 5,327,909 A | 7/1994 | Kiser et al. |
| 5,385,579 A * | 1/1995 | Helland ...................... 607/130 |
| 5,431,649 A | 7/1995 | Mulier et al. |
| 5,540,727 A | 7/1996 | Tockman et al. |
| 5,584,868 A | 12/1996 | Salo et al. |
| 5,618,287 A | 4/1997 | Fogarty et al. |
| 5,643,330 A | 7/1997 | Holsheimer et al. |
| 5,683,447 A | 11/1997 | Bush et al. |
| 5,716,392 A | 2/1998 | Bourgeois et al. |
| 5,728,140 A * | 3/1998 | Salo et al. ...................... 607/9 |
| 5,800,465 A | 9/1998 | Thompson et al. |
| 5,895,416 A | 4/1999 | Barreras, Sr. et al. |
| 5,916,243 A | 6/1999 | KenKnight et al. |
| 5,951,543 A * | 9/1999 | Brauer ........................ 606/10 |
| 6,285,906 B1 * | 9/2001 | Ben-Haim et al. .............. 607/4 |
| 2002/0082651 A1* | 6/2002 | Stahmann et al. .............. 607/9 |
| 2002/0173826 A1* | 11/2002 | Lincoln et al. .................. 607/9 |
| 2003/0078671 A1 | 4/2003 | Lesniak et al. |
| 2003/0199938 A1 | 10/2003 | Smits et al. |

FOREIGN PATENT DOCUMENTS

| WO | WO9725098 | * 7/1997 |
|---|---|---|
| WO | 0222206 | 3/2002 |

* cited by examiner

*Primary Examiner* — Niketa Patel
*Assistant Examiner* — Rex R Holmes
(74) *Attorney, Agent, or Firm* — Reed A. Duthler; Stephen W. Bauer

(57) ABSTRACT

A method for pacing a left ventricle of a heart includes delivering a pacing pulse via a first electrode to activate a first papillary muscle and another pacing pulse via a second electrode to activate a second papillary muscle.

19 Claims, 2 Drawing Sheets

PAPILLARY MUSCLE STIMULATION

RELATED APPLICATIONS

This application is a continuation-in-part of U.S. Application 60/333,762, which is incorporated by reference in its entirety herein; U.S. Application 60/333,762 was filed Nov. 29, 2001 and converted from a provisional to a non-provisional application on Nov. 29. 2002, under Ser. No. 10/360, 765 now abandoned. Furthermore, cross-reference is hereby made to the commonly assigned related U.S. application Ser. No. 10/832,738 entitled "Trans-septal Pacing Method and Apparatus" filed concurrently herewith and incorporated by reference in its entirety herein.

TECHNICAL FIELD

The present invention relates to implantable medical devices and more particularly to left-ventricular papillary muscle stimulation.

BACKGROUND

Patients with poor atrio-ventricular conduction or poor sinus node function typically receive pacemaker implants to restore a normal heart rate. For another set of patients suffering from left bundle branch block (LBBB), left ventricular pacing and/or bi-ventricular pacing has been shown to significantly improve cardiac hemodynamics and quality of life. However, some studies have shown that traditional pacing from a right ventricular (RV) apex can impair cardiac pumping performance. In some instances, ventricular wall abnormalities (ventricular remodeling) resulting from RV apical pacing have also been observed. So, alternative sites have been found where pacing can cause an electrical activation sequence similar to that in a normally activated heart and thus contribute to improved cardiac pump function.

From the literature there appear to be three major characteristics of normal cardiac electrical activation: 1.) Earlier activation of the left ventricle than right ventricle; 2.) Earlier endocardial activation than epicardial activation in left ventricular free wall; and 3.) Earlier activation in the apex than in the base of both ventricles. It has been found that a site of earliest activation occurs in the endocardium of the left ventricle along a lower portion of the inter-ventricular septum (i.e. near the apex) where the septum joins with the anterior wall of the heart and in close proximity to bases of left ventricular papillary muscles. Proper timing of papillary muscle activation is necessary to cause closure of the mitral valve prior to main left ventricular contraction so that regurgitation is prevented.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following description is exemplary in nature and is not intended to limit the scope, applicability, or configuration of the invention in any way. Rather, the following description provides a practical illustration for implementing exemplary embodiments of the invention.

Figure 1:
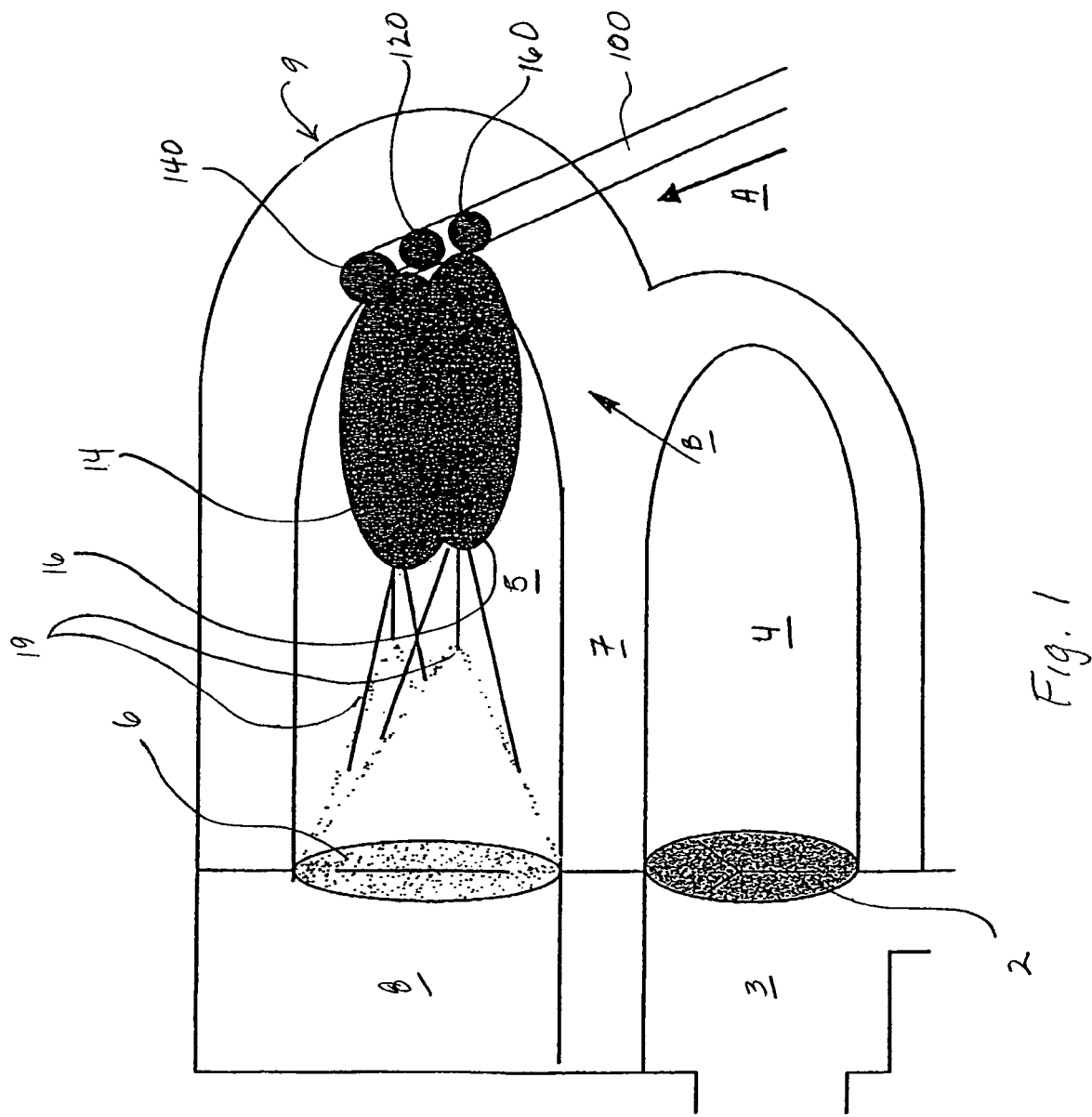
FIG. 1 is a schematic section through a heart wherein a pacing lead according to one embodiment of the present invention is implanted.

FIG. 1 is a schematic section through a heart wherein a distal portion of a pacing lead 100 according to one embodiment of the present invention is implanted. Materials forming lead 100 and an arrangement of conductors, insulation and connector components, which couple lead 100 to a pacemaker device (not shown), may all conform to that of standard pacing leads. FIG. 1 illustrates the distal portion of lead 100 extending through a ventricular apex 9 of a left ventricle 5 having been inserted epicardially per arrow A in an anterior to posterior direction; lead 100 includes a first electrode 140 that has been positioned in proximity to a posterior papillary muscle 14 and a second electrode 160 that has been positioned in proximity to an anterior papillary muscle 16. Papillary muscles 14 and 16 are joined to a mitral valve 6 via chordae tendineae 19 and, according to some embodiments of the present invention, electrodes 140 and 160 are positioned to deliver pacing pulses in proximity to papillary muscles in order to activate mitral valve closure prior to left ventricular contraction and thus prevent regurgitation of blood back into a left atrium 8.

According to an alternate method of the present invention, papillary muscle conduction is isolated from that in the surrounding myocardium by means of ablation; such isolation may enable pacing to better control papillary action independent of myocardial activation. Means described herein for delivering lead 100 may also be used to deliver an ablation catheter to the site of the papillary muscles for ablating around the base thereof prior to pacing with implanted lead 100.

FIG. 1 further illustrates lead 100 including a third electrode 120 located in between first electrode 140 and second electrode 160; according to the illustrated embodiment, third electrode 120 functions as an anode and forms a first bipolar pair with first electrode 140 to pace and sense in proximity to posterior papillary muscle 14 and a second bipolar pair with second electrode 160 to pace and sense in proximity to anterior papillary muscle 16. According to an alternate embodiment of the present invention, third electrode 120 is not included and first and second electrodes 140 and 160 operate either in a unipolar mode or are adapted to alternate between polarities for bipolar operation such that, in one point in time, first electrode 140 is a cathode and second electrode 160 an anode for pacing in proximity to posterior papillary muscle 14, and at another point in time, second electrode 160 is the cathode and first electrode 140 is the anode for pacing in proximity to anterior papillary muscle 16. Furthermore, according to one embodiment, pacing pulses, delivered via first and second electrodes 140 and 160 (unipolar or bipolar, with third electrode 120), are delivered simultaneously, while, according to an alternate embodiment, the pacing pulses are delivered with a delay between the pulses, the delay dependent upon local tissue depolarization speed and electrical—mechanical coupling characteristics. State of the art electrode features including surface areas, macro and micro, and surface structure and treatments may be incorporated into some embodiments of the present invention.

FIG. 1 also illustrates first electrode sized to serve as an anti-retraction feature, that is electrode 140 is oversized or includes an outer surface protruding radially from an adjacent portion of lead 100 just proximal to electrode 140. Although not illustrated in FIG. 1 lead 100 may further include a tine-like structure just distal to first electrode 140; such a structure is described in aforementioned co-pending application entitled "Trans-septal Pacing Method and Apparatus" filed concurrently herewith and incorporated by reference.

An alternate endocardial approach for insertion of the distal end of lead 100 is illustrated in part in FIG. 1. Lead 100 may be passed through a right atrium 3 and a tricuspid valve 2 into a right ventricle 4 via a standard transvenous route, which may accessed by cephalic cut-down or subclavian stick, and the distal portion of lead 100 inserted through an interventricular septal wall 7 toward left ventricular apex 9, approximately via arrow B, to position electrodes 140, 160, and 120 (if present) in proximity to papillary muscles 14 and 16; a curved puncture needle may be required to create an appropriate pathway for lead insertion.

Figure 2:
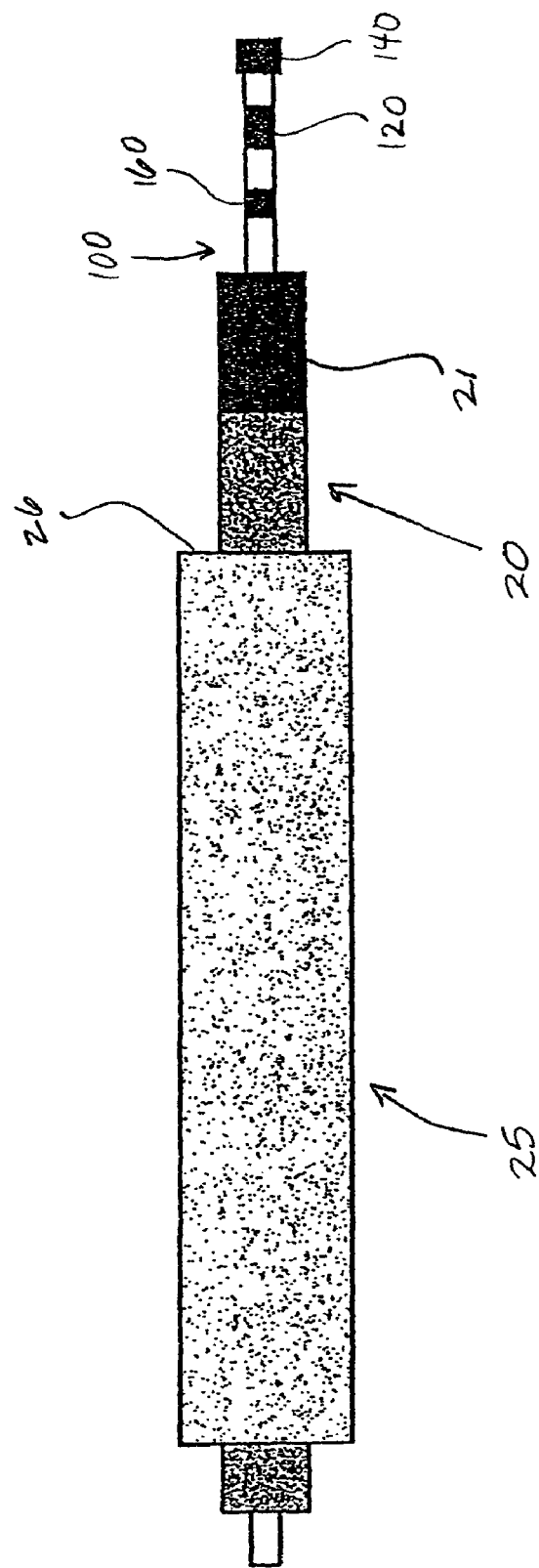
FIG. 2 is a plan view of a distal portion of a delivery system according to an embodiment of the present invention.

FIG. 2 is a plan view of a distal portion of a delivery system according to an embodiment of the present invention. FIG. 2 illustrates the delivery system including a guiding catheter 25, a septal puncture needle 20 slideably received within the guiding catheter 25, and lead 100 slideably received within puncture needle 20. According to the illustrated embodiment, catheter 25 would be positioned, via a thoroscopic port, against an endocardial surface of left ventricular apex 9 (FIG. 1) so that needle 20, passing through catheter 25 may puncture through apex 9; guiding catheter 25 may be of a type of guiding catheter well known to those skilled in the art, which is constructed having a shape enabling positioning for a selected puncture site and a stiffness sufficient to provide backup support for puncturing. Once a passageway is established by needle 20, lead 100 is passed through and positioned as illustrated in FIG. 1. According to other embodiments of the present invention, an alternate method for passing lead 100 through apex 9 includes first piercing through apex 9 with a tool to make a bore and then removing the tool to pass lead 100 through the bore. According to yet another embodiment, lead 100 includes a piercing tip so that lead 100, reinforced by an internal stiffening stylet may pierce through apex 9 without need for an independent piercing tool.

FIG. 2 further illustrates an electrode 21 coupled in proximity to a distal end of needle 20 which may be used to sense and/or pace as needle 20 passes through apex 9. Once lead 100 has been passed through apex 9, needle 20 is pulled back out from apex 9 and guiding catheter 25 is removed from the access port; then lead may be coupled to a pacemaker device positioned in an abdominal pocket according to means known to those skilled in the art.

It may be appreciated that various modifications and changes can be made to the various embodiments described herein without departing from the scope of the invention as set forth in the appended claims.

What is claimed is:

1. A method for pacing a left ventricle of a heart having an apex wall with an outer surface, comprising the steps of:
   providing a lead having a first electrode and a second electrode on a distal portion;
   inserting the distal portion of the lead into the apex wall such that the distal portion extends into the apex wall of a left ventricle of a heart;
   the first electrode being beneath the outer surface of the left ventricle and in proximity to a base of a first left ventricular papillary muscle;
   the second electrode being beneath the outer surface of the left ventricle and in proximity to a base of a second left ventricular papillary muscle; and
   producing activation in the apex of the left ventricle by delivering a pacing pulse via the first electrode in close proximity to the first papillary muscle so as to activate the first papillary muscle and delivering another pacing pulse via the second electrode in close proximity to the second papillary muscle so as to separately activate the second papillary muscle, the pacing pulses being delivered to the first and second electrodes with a timing relationship that causes closure of a mitral valve prior to a main left ventricular contraction.

2. The method of claim 1, wherein the pacing pulses, delivered via the first and second electrodes, are delivered simultaneously.

3. A method for pacing a left ventricle of a heart having an apex wall with an outer surface, comprising the steps of:
   providing a lead having a first electrode and a second electrode on a distal portion;
   inserting the distal portion of the lead into the apex wall such that the distal portion extends into the apex wall of a left ventricle of a heart;
   the first electrode being beneath the outer surface of the left ventricle and in proximity to a base of a first left ventricular papillary muscle;
   the second electrode being beneath the outer surface of the left ventricle and in proximity to a base of a second left ventricular papillary muscle; and
   producing activation in the apex of the left ventricle by delivering a pacing pulse via the first electrode in close proximity to the first papillary muscle so as to activate the first papillary muscle and delivering another a second pacing pulse via the second electrode in close proximity to the second papillary muscle so as to activate the second papillary muscle, the pacing pulses being delivered to the first and second electrodes with a timing relationship that causes closure of a mitral valve prior to a main left ventricular contraction, wherein the pacing pulses, delivered via the first and second electrodes are delivered with a delay between the pulses.

4. A method for pacing a left ventricle of a heart having an apex wall with an outer surface, comprising the steps of:
   providing a lead having a first electrode and a second electrode on a distal portion;
   inserting the distal portion of the lead into the apex wall such that the distal portion extends into the apex wall of a left ventricle of a heart;
   the first electrode being beneath the outer surface of the left ventricle and in proximity to a base of a first left ventricular papillary muscle;
   the second electrode being beneath the outer surface of the left ventricle and in proximity to a base of a second left ventricular papillary muscle; and
   producing activation in the apex of the left ventricle by delivering a pacing pulse via the first electrode in close proximity to the first papillary muscle so as to activate the first papillary muscle and delivering another a second pacing pulse via the second electrode in close proximity to the second papillary muscle so as to activate the second papillary muscle, the pacing pulses being delivered to the first and second electrodes with a timing relationship that causes closure of a mitral valve prior to a main left ventricular contraction, wherein the distal portion of the lead further includes a third electrode coupled thereto in between the first electrode and the second electrode in order that the third electrode forms a first bipolar pair with the first electrode and a second bipolar pair with the second electrode.

5. The method of claim 1, wherein the distal portion of the pacing lead is inserted into the left ventricular apex wall from an epicardial approach.

6. The method of claim 5, wherein the step of inserting is preceded by a step of passing a guiding catheter through a thorascopic access port such that a distal end of the guiding catheter contacts the left ventricular apex to form a conduit for passage of the distal portion of the pacing lead.

7. The method of claim 5, wherein the step of inserting is preceded by a step of puncturing through the left ventricular apex wall with a puncture needle.

8. The method of claim 7, wherein the distal portion of the lead is inserted into the left ventricular apex wall through a lumen of the puncture needle.

9. The method of claim 1, wherein the distal portion of the pacing lead is inserted into the left ventricular apex wall from a right ventricle via an endocardial trans-septal approach.

10. A method for pacing a left ventricle of a heart having an apex wall with an outer surface, comprising the steps of:
 providing a lead having a first electrode and a second electrode on a distal portion;
 inserting the distal portion of the lead into the apex wall such that the distal portion extends into the apex wall of a left ventricle of a heart;
 the first electrode being beneath the outer surface of the left ventricle and in proximity to a base of a first left ventricular papillary muscle;
 the second electrode being beneath the outer surface of the left ventricle and in proximity to a base of a second left ventricular papillary muscle; and
producing activation in the apex of the left ventricle by delivering a pacing pulse via the first electrode in close proximity to the first papillary muscle so as to activate the first papillary muscle and delivering another a second pacing pulse via the second electrode in close proximity to the second papillary muscle so as to activate the second papillary muscle, the pacing pulses being delivered to the first and second electrodes with a timing relationship that causes closure of a mitral valve prior to a main left ventricular contraction, further comprising the step of isolating conduction within the first and second left ventricular papillary muscles from myocardial conduction of the left ventricle prior to delivering the pacing pulses.

11. The method of claim 10, wherein the means for isolating comprises ablation.

12. The method of claim 1, wherein the first electrode is positioned in proximity to the base of a posterior left ventricular papillary muscle and the second electrode is positioned in proximity to the base of an anterior left ventricular papillary muscle.

13. The method of claim 12, wherein pacing pulses are delivered to the posterior left ventricular papillary muscle and to the anterior left ventricular papillary muscle with a timing relationship that causes closure of a mitral valve prior to a main left ventricular contraction, whereby regurgitation is prevented.

14. A method for pacing a left ventricle of a heart having an apex wall with an outer surface, comprising the steps of:
 providing a lead having a first electrode and a second electrode on a distal portion;
 inserting the distal portion of the lead into the apex wall such that the distal portion extends into the apex wall of a left ventricle of a heart;
 the first electrode being beneath the outer surface of the left ventricle and in proximity to a base of a first left ventricular papillary muscle;
 the second electrode being beneath the outer surface of the left ventricle and in proximity to a base of a second left ventricular papillary muscle; and
 producing activation in the apex of the left ventricle by delivering a pacing pulse via the first electrode in close proximity to the first papillary muscle so as to activate the first papillary muscle and another pacing pulse via the second electrode in close proximity to the second papillary muscle so as to separately activate the second papillary muscle,
 wherein the first electrode is positioned in proximity to the base of a posterior left ventricular papillary muscle and the second electrode is positioned in proximity to the base of an anterior left ventricular papillary muscle.

15. A method for pacing a left ventricle of a heart comprising the steps of:
 positioning a first electrode in proximity to a base of a first left ventricular papillary muscle;
 positioning a second electrode in proximity to a base of a second left ventricular papillary muscle; and
 delivering a pacing pulse via the first electrode which activates the first papillary muscle and another pacing pulse via the second electrode which separately activates the second papillary muscle.

16. The method of claim 15, wherein the pacing pulses, delivered via the first and second electrodes, are delivered simultaneously.

17. The method of claim 1, wherein the pacing pulses, delivered via the first and second electrodes, are delivered with a delay between the pulses.

18. The method of claim 1, further comprising the step of isolating conduction within the first and second left ventricular papillary muscles from myocardial conduction of the left ventricle prior to delivering the pacing pulses.

19. The method of claim 10, wherein the means for isolating comprises ablation.

* * * * *